(12) United States Patent
King

(10) Patent No.: US 12,575,965 B2
(45) Date of Patent: Mar. 17, 2026

(54) METHODS AND DEVICES FOR APPLYING HYPOTHERMIC THERAPY TO A HUMAN AUDITORY SYSTEM

(71) Applicant: Restorear Devices, LLC, Bozeman, MT (US)

(72) Inventor: Curtis S. King, Bozeman, MT (US)

(73) Assignee: Restorear Devices, LLC, Kirkland, WA (US)

( * ) Notice: Subject to any disclaimer, the term of this patent is extended or adjusted under 35 U.S.C. 154(b) by 231 days.

(21) Appl. No.: 18/291,455

(22) PCT Filed: Aug. 2, 2021

(86) PCT No.: PCT/US2021/044150

§ 371 (c)(1),
(2) Date: Jan. 23, 2024

(87) PCT Pub. No.: WO2023/014342

PCT Pub. Date: Feb. 9, 2023

(65) Prior Publication Data

US 2024/0207090 A1 Jun. 27, 2024

(51) Int. Cl.
*A61F 7/12* (2006.01)
*A61F 7/00* (2006.01)

(52) U.S. Cl.
CPC ........ *A61F 7/12* (2013.01); *A61F 2007/0005* (2013.01); *A61F 2007/0093* (2013.01)

(58) Field of Classification Search
CPC ...... A61F 2007/0004; A61F 2007/0005; A61F 2007/00093; A61F 7/12
See application file for complete search history.

(56) References Cited

U.S. PATENT DOCUMENTS

| | | | | |
|---|---|---|---|---|
| 5,868,682 | A * | 2/1999 | Combs | G01H 15/00 |
| | | | | 600/559 |
| 8,840,565 | B2 * | 9/2014 | Keefe | A61B 5/121 |
| | | | | 600/559 |
| 11,896,826 | B1 * | 2/2024 | Black | A61F 7/007 |
| 2013/0310907 | A1 * | 11/2013 | Rogers | A61F 7/007 |
| | | | | 607/113 |
| 2016/0219965 | A1 * | 8/2016 | Sansone | A42B 3/285 |
| 2016/0346117 | A1 * | 12/2016 | Rogers | A61F 7/12 |
| 2019/0269336 | A1 * | 9/2019 | Perkins | A61B 5/291 |
| 2020/0100938 | A1 * | 4/2020 | King | A61F 7/10 |
| 2021/0137730 | A1 * | 5/2021 | Smith | A61F 7/007 |

FOREIGN PATENT DOCUMENTS

WO 2014093875 6/2014

* cited by examiner

*Primary Examiner* — Joseph A Stoklosa
(74) *Attorney, Agent, or Firm* — Brian C. Trask

(57) ABSTRACT

An assembly 100 to provide thermal therapy to a human auditory system includes a thermal transducer 125, a stimulus transducer 120, 135, a receiver 130, and a processing device 145. Some or all of the individual components may be carried in headwear. The thermal transducer 125 applies hypothermic temperature conditions to an area of the head near an ear. The stimulus transducer 120, 135 applies a stimulus signal, and the receiver 130 detects otoacoustic emission (OAE) responsive to the stimulus signal. The processor 145 compares the received OAE signal to a reference. Discrepancy between the OAE and reference is used in a feedback loop to control operation of the system 100.

20 Claims, 20 Drawing Sheets

125

216

220

218

125

216

218

220

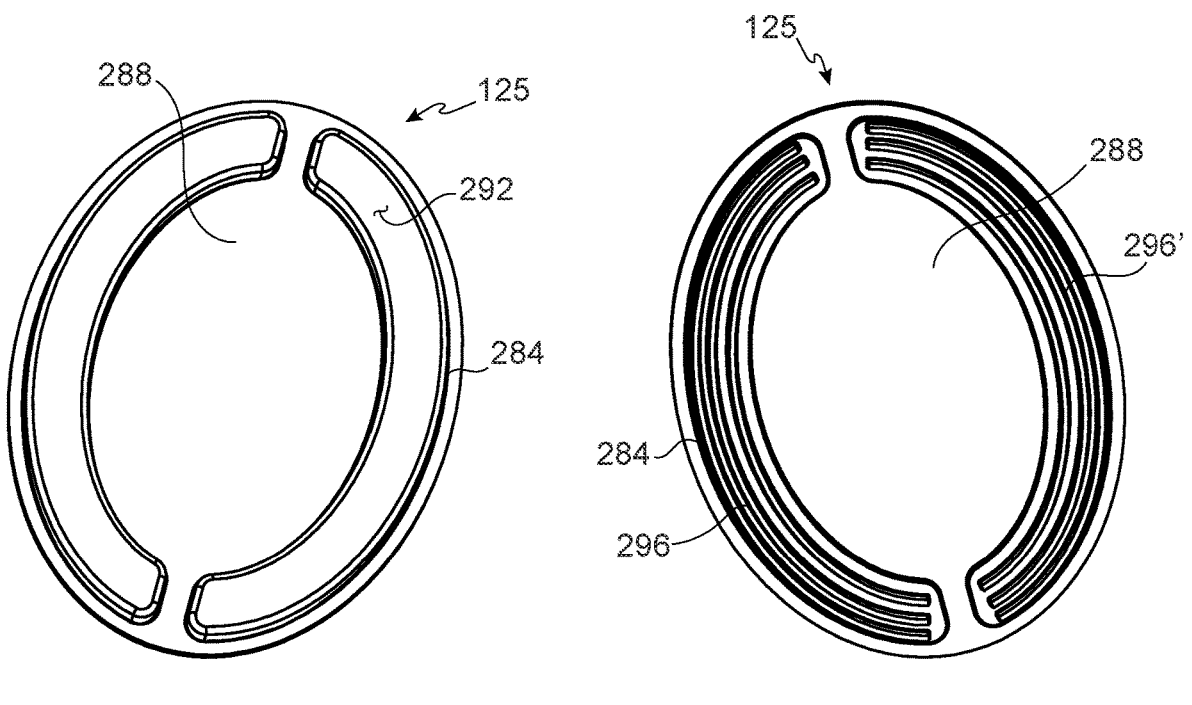
Fig. 16
Fig. 17
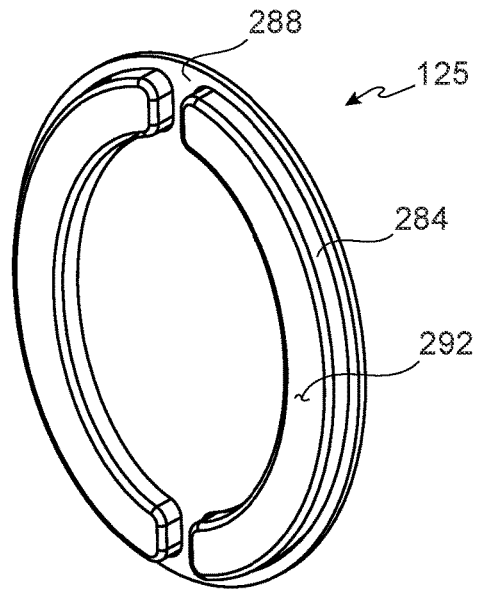
Fig. 18
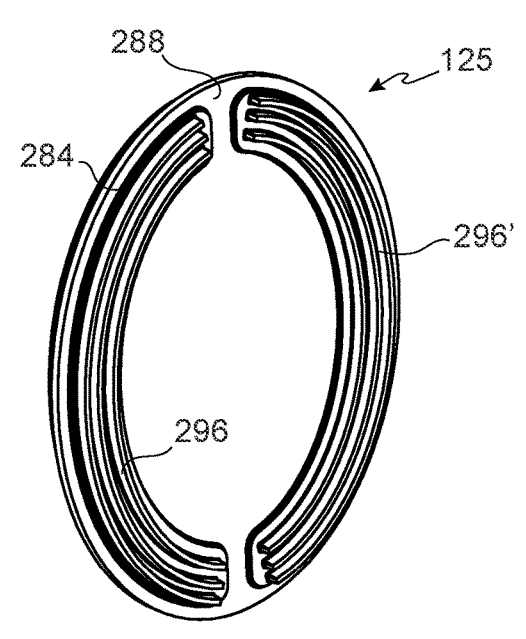
Fig. 19

218

125

218

125

METHODS AND DEVICES FOR APPLYING HYPOTHERMIC THERAPY TO A HUMAN AUDITORY SYSTEM

PRIORITY CLAIM

This application is a National Stage filing of International Application Serial No. PCT/US2021/044150, filed 2 Aug. 2021, for "METHODS AND DEVICES FOR APPLYING HYPOTHERMIC THERAPY TO A HUMAN AUDITORY SYSTEM"

TECHNICAL FIELD

This invention relates to devices and methods for applying thermal therapy to a human subject.

BACKGROUND

Mild Therapeutic Hypothermia (MTH) has been shown to have benefits to human tissue and various physiological systems. Recently, it has been shown that MTH has otoprotective potential for the organs and structures of the human inner and outer ear. For example, the application of MTH during and after cochlear implant surgical procedures has been shown to improve procedural outcomes by improved preservation of residual (ie, natural) hearing. Research studies have also shown the potential for MTH to be useful as a therapy to offset the effects of noise induced hearing loss (NIHL).

At the time of this writing, hypothermia therapy to correct auditory trauma is in its infancy. Devices or systems to perform such therapy are not commercially available. It would be an improvement to provide a system to facilitate treatment of human auditory system damage by way of thermal therapy, including localized hypothermia therapy.

DISCLOSURE OF THE INVENTION

The present invention provides an apparatus and method for applying thermal therapy to the auditory system of a human patient. A currently preferred apparatus may be embodied in an assembly of cooperating elements. One such assembly includes a thermal energy transducer, a stimulus transducer, a receiver transducer, and a processor operably disposed in-circuit with the thermal energy transducer, stimulus transducer, and receiver transducer. Sometimes, the assembly may include a dosing mechanism to dispense a therapeutic drug to the patient as a portion of a thermal therapy program.

A thermal energy transducer can cause flow of thermal energy toward or away from a portion of the head of a human patient in the vicinity of an ear of the patient. Workable thermal energy transducers include active and passive devices. An ice pack is exemplary of a passive device. In contrast, a thermoelectric transducer is exemplary of an active device. Workable thermoelectric devices include Peltier heat pumps. In contrast to an ice pack, a currently preferred thermal energy transducer can provide a controlled: flow rate, size and/or location of a heat transfer zone, and/or total amount of thermal energy for transfer to or from the head.

An ice pack is an example of a workable thermal energy transducer. Another thermal energy transducer within contemplation includes an electrically controllable thermal source or sink. Typically, at least one thermal energy transducer is disposed in association with each ear of the patient.

It is within contemplation that a plurality of thermal sources or sinks may be configured to at least partially circumscribe an ear canal of the patient. Further, it can be advantageous if a plurality of the thermal sources or sinks are individually controllable. Also, in some cases, a workable thermal energy transducer may be configured to provide a heat transfer zone disposed inside an ear canal.

A stimulus transmitter can impart a stimulus signal to a portion of the head of the patient. Desirably, a stimulus signal is received by inner structure of the ear. A stimulus signal can be a sound wave that is transmitted through the ear canal toward the eardrum. An alternative stimulus signal may be imparted by a mechanical device and conducted through bone and/or tissue toward the ear center. Exemplary mechanical stimulus transmitters include an audio speaker, and/or piezo and mechanical vibrating mechanisms of various sorts.

A receiver transducer can receive an otoacoustic emission (OAE) from the ear responsive to the stimulus signal. One workable receiver transducer includes a microphone.

There are three types of OAEs of clinical interest: stimulus frequency OAE; transient-evoked OAE; and distortion product OAE. Stimulus Frequency OAEs (SFOAEs) are measured during the application of a pure tone stimulus and are detected by the vectorial difference between the stimulus waveform and the recorded waveform (which consists of the sum of the stimulus and the OAE). Transient-evoked OAEs (TEOAEs or TrOAEs) are evoked using a tone burst (brief duration pure tone) stimulus. The evoked response from a tone burst will elicit a response from the region that has the same frequency as the pure tone. Distortion product OAEs (DPOAEs) are evoked using a pair of primary tones $f_1$ and $f_2$ with particular intensity and ratio ($f_1:f_2$). The evoked responses from these stimuli occur at frequencies ($f_d$) mathematically related to the primary frequencies, with the two most prominent being $f_d=2f_1-f_2$ (the "cubic" distortion tone, commonly used for hearing screening) because they produce the most robust emission and $f_d=f_1-f_2$ (the "quadratic" distortion tone, or simple difference tone.

A processor can operate a program to control one or more action of the assembly. Desirably, the processor operates in-part to compare a received OAE signal to an expected reference signal. Any discrepancy between the OAE and reference may be used in a feedback loop to control flow of thermal energy between a thermal energy transducer and the patient.

Sometimes, one or more elements of the assembly may be embodied in, or carried by headwear. One exemplary headwear is configured upon installation to dispose an ear pinna inside an ear cup such that a portion of a heat transfer element of a thermal energy transducer is disposed between the pinna and a temporal bone of the patient.

The invention may be embodied as a first method to apply thermal therapy to a human patient. One such first method includes providing a thermal therapy system configured to apply thermal therapy to a portion of a human head in the vicinity of at least one ear. A workable thermal therapy system includes a device to transmit thermal energy to, or receive thermal energy from, a portion of the head of a human patient in the vicinity of an ear of the patient; a transmitter to impart a stimulus to a portion of the head; a receiver to detect a signal comprising acoustic emission from the ear responsive to the stimulus; and a processing element disposed in operable connection with the device, transmitter, and receiver to compare the signal to a reference. The first method may further include disposing a heat transfer portion of the device in operable registration with a temporal bone of the patient; using the transmitter to impart the stimulus; using the receiver to receive the signal; using the processing element to compare a received signal to the reference and create a feedback signal, the feedback signal being based at least in-part upon deviation of the received signal from the reference; and incorporating the feedback signal into operation of the system to control application of thermal therapy to the patient.

The invention may be embodied as a second method to apply thermal therapy to a human patient. One such second method includes the step of providing a thermal therapy system. A workable thermal therapy system may be configured to apply thermal therapy to a portion of a human head in the vicinity of at least one ear. A preferred thermal therapy system includes headwear carrying a device configured to transmit thermal energy to, or receive thermal energy from, a portion of the head of a human patient in the vicinity of an ear of the patient.

Desirably the headwear also carries a transmitter to impart a first signal as a stimulus to a portion of the head, and a first receiver to detect or receive a second signal comprising acoustic emission from the ear responsive to the stimulus. The first signal may include a sound wave transmitted through air. However, the first signal can applied by the transmitter to structure of the head for conduction into the ear through a solid medium, such as flesh and/or bone.

A processing element is disposed in operable connection with the device, transmitter, and receiver to compare a received second signal to a reference. A workable first reference can include expected transient-evoked OAE or expected distortion product OAE. The expected signals may be empirically determined.

The second method further includes installing the headwear onto the head of the patient to dispose a heat transfer area of the device in operable registration with a temporal bone of the patient, using the transmitter to impart the first signal, using the first receiver to monitor for presence of the second signal, comparing a received second signal to a first reference to create a first feedback signal based at least in-part upon deviation of the received second signal from the first reference, and incorporating the first feedback signal into operation of the system to apply thermal therapy to the patient.

A workable system may further include a second receiver capable of detecting a third signal, the third signal to indicate a state or condition of a physiologic variable selected from the group consisting of heart rate, blood pressure, EKG/ECG, body or skin temperature, blood/oxygen saturation, and skin moisture. In that case, the method may further include acquisition of the third signal and comparison of the third signal to a corresponding physiologic metric reference to modify the first feedback signal or to create a second feedback signal for operation of the system based in-part upon deviation of the received third signal from the corresponding physiologic metric reference. The second feedback signal can used by the system as a control input for injection of a chemical agent into the patient. So, the method can further include using the system to inject the chemical agent into the patient.

A method may include modifying thermal therapy applied to the patient based, in-part, on departure of the second signal or the third signal from its corresponding reference over a period of time.

Sometimes, the step of installing the headwear onto the head of the patient includes disposing a thermal conveyance portion of the device in contact with an area located between a pinna of the patient and the patient's skull. Also, the step of installing the headwear onto the head of the patient can include folding a pinna of a patient's ear to facilitate entrance of the pinna into an ear cup during placement the ear cup of the headwear onto the head for engagement of a cup's heat transfer surface around a portion of the ear.

BRIEF DESCRIPTION OF THE DRAWINGS

In the drawings, which illustrate what are currently regarded as the best modes for carrying out the invention and in which like reference numerals refer to like parts in different views or embodiments:

FIG. 16 is a front view of a portion of an ear cup;

FIG. 17 is a rear view of the assembly in FIG. 16;

FIGS. 18 and 19 are views in perspective of the devices in FIGS. 16 and 17, respectively;

MODES FOR CARRYING OUT THE INVENTION

Figure 1:
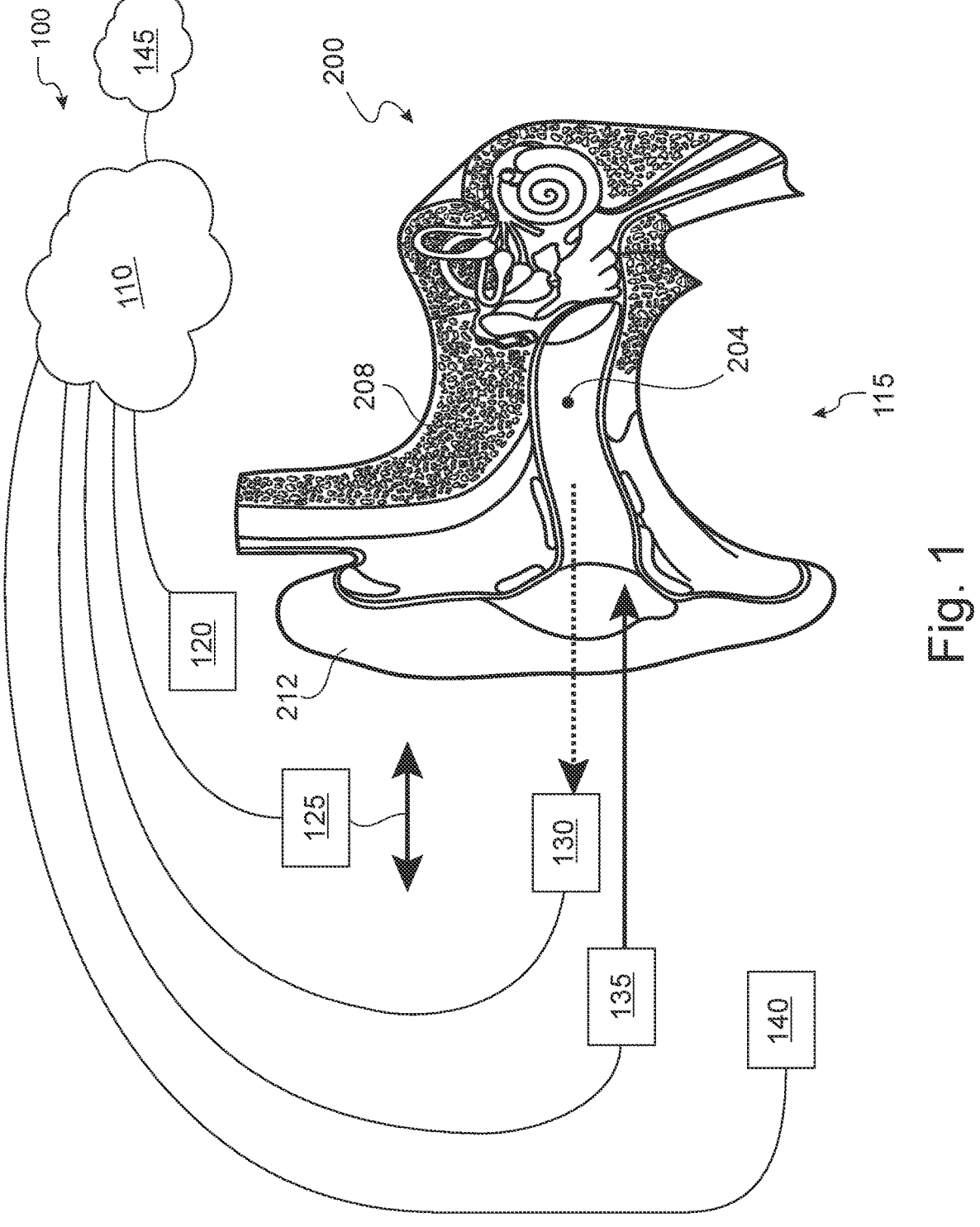
FIG. 1 is a schematic of a general arrangement according to certain principles of the invention.

A generalized schematic of an embodiment of a system according to certain principles of the instant invention is indicated generally at 100 in FIG. 1. Embodiment 100 provides a system for performing thermal therapy on a human patient. Embodiment 100 can include an assembly 110 including a variable number of components configured and arranged to operably interface with a portion of the head of the patient, generally 115. In certain cases, an assembly 110 may provide all, or substantially all, of the elements required in a system 100. Sometimes, one or more element may be provided as a stand-alone component of a system 100.

As illustrated, this embodiment 100 may optionally include a stimulus transducer 120 to mechanically apply a stimulus to physical structure of the head 115. A workable stimulus transducer can impart a signal toward the inner ear through bone conduction. Exemplary transducers 120 include piezo-based, eccentric rotating, oscillating, or other vibration-inducing transducers. A thermal transducer 125 may be configured in a variety of specific ways to impart a change in temperature, or to maintain a steady temperature of a portion of the head 115. Transducer 130 is operable to detect an audible emission from the head 115. Of particular interest is otoacoustic emission (OAE) responsive to a stimulus. A microphone is an exemplary embodiment of a transducer 130. An optional sonic transducer 135 is operable to impart a sound wave signal toward the head 115. A speaker is an example of a workable transducer 135.

One or more additional transducer 140 may also be included in an assembly 110. A workable such transducer 140 may impart a stimulus to the patient, monitor a physical characteristic of the patient or a system element, administer a medicament to the patient, or detect an output from the patient, as desired. One transducer 140 within contemplation is a temperature sensor. Another transducer 140 within contemplation is a dosing syringe to dispense a medicament into a patient. A processing device 145 is included to control operation of the embodiment 100.

Preferred embodiments 100 are configured to cause a change in temperature of a portion of the head 115, typically to reduce a temperature in the vicinity of the inner ear, generally 200. Temperature in the vicinity of the inner ear 200 can advantageously be influenced by a heat transfer device located inside the ear canal 204. Logically, the ear canal 204 provides the shortest and most direct path. Alternatively, a heat transfer device may be positioned to conduct thermal energy by way of the temporal bone 208. In the latter case, it is best practice to transmit thermal energy along a shortest path adjacent to the ear canal 204. Therefore, a heat transfer device is desirably disposed between the pinna 212 and the temporal bone 208.

In general, this disclosure will make reference to an ear flap as the pinna. An ear flap can also be defined as that portion of the pinna of an ear that is cantilevered from a base disposed near the ear canal 204 and projects radially outward to overlap the skull. If intended below, a more specific or alternative meaning for the term "pinna" will be made expressly or in context.

Figure 2:
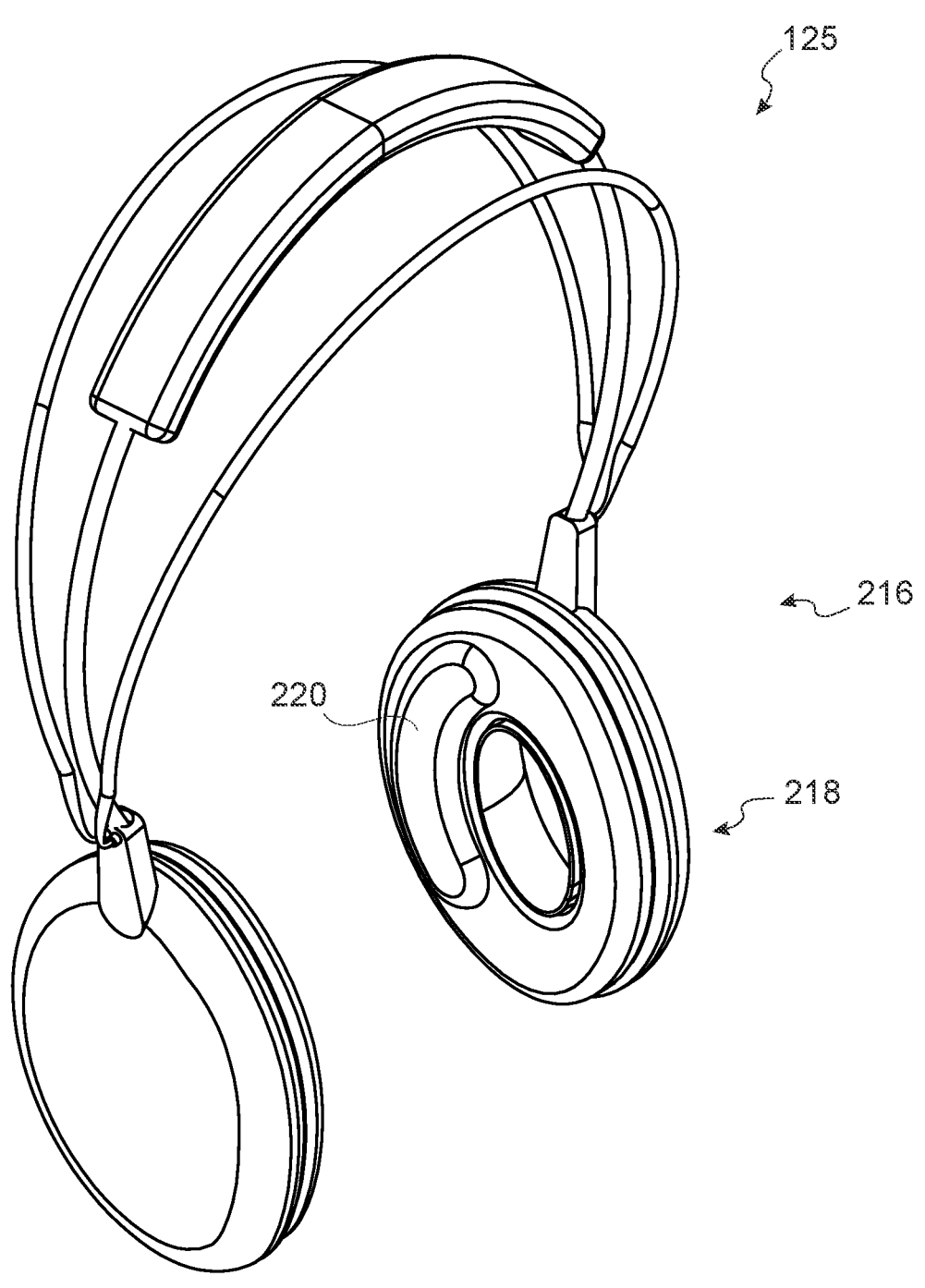
FIG. 2 is a view in perspective of headwear workable for certain embodiments.
Figure 3:
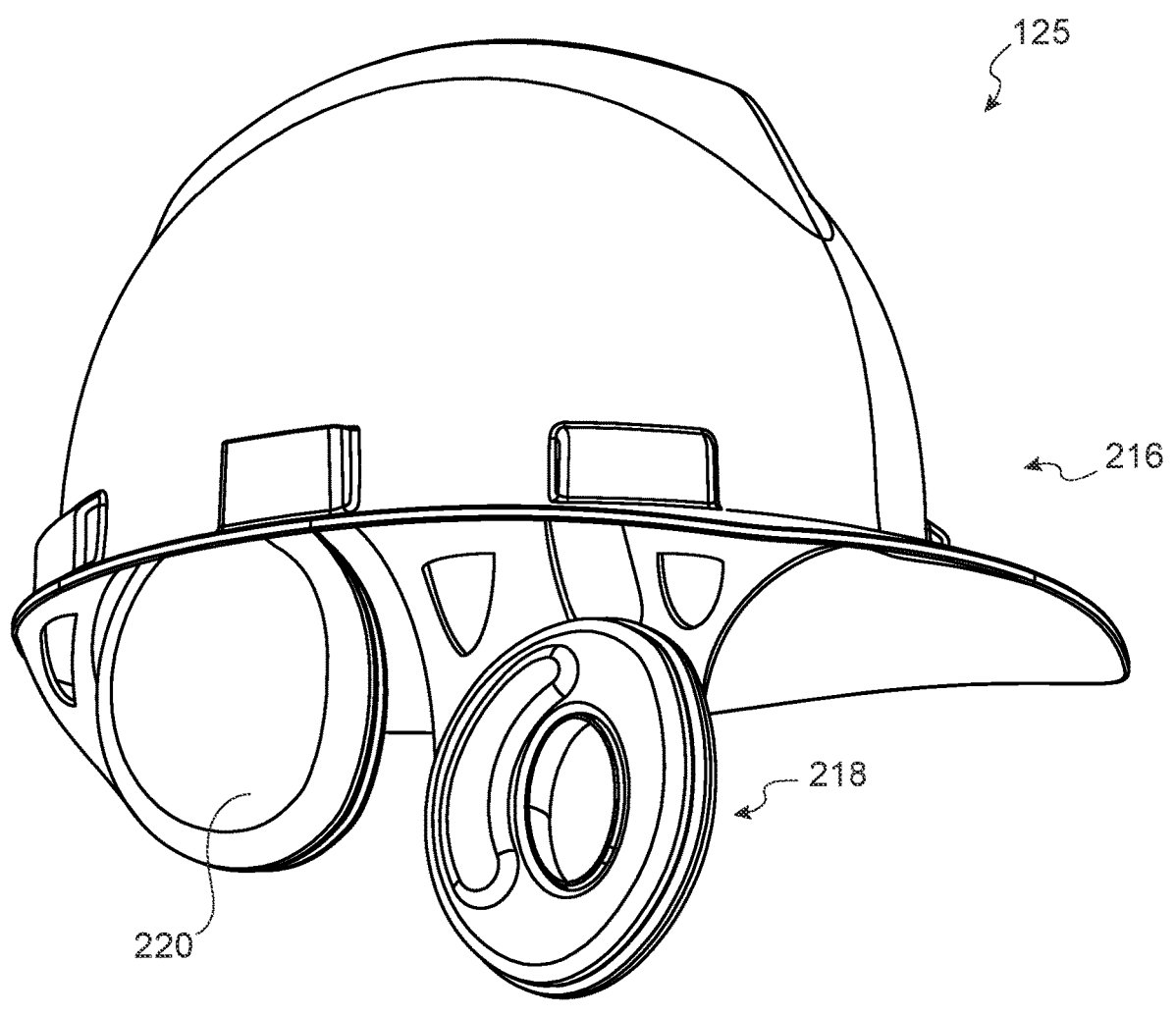
FIG. 3 is a view in perspective of headwear workable for certain embodiments.
Figure 4:
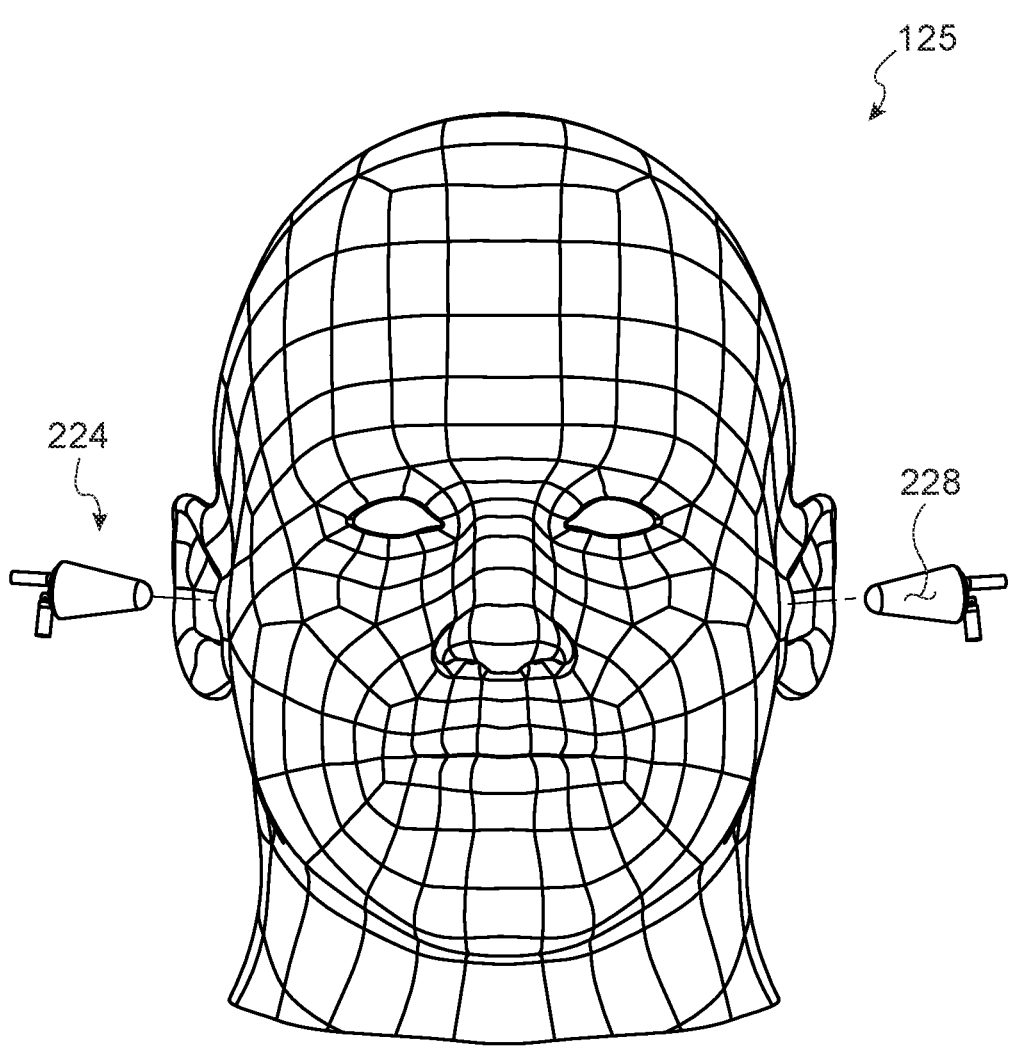
FIG. 4 is a view in elevation of headwear workable for certain embodiments.
Figure 5:
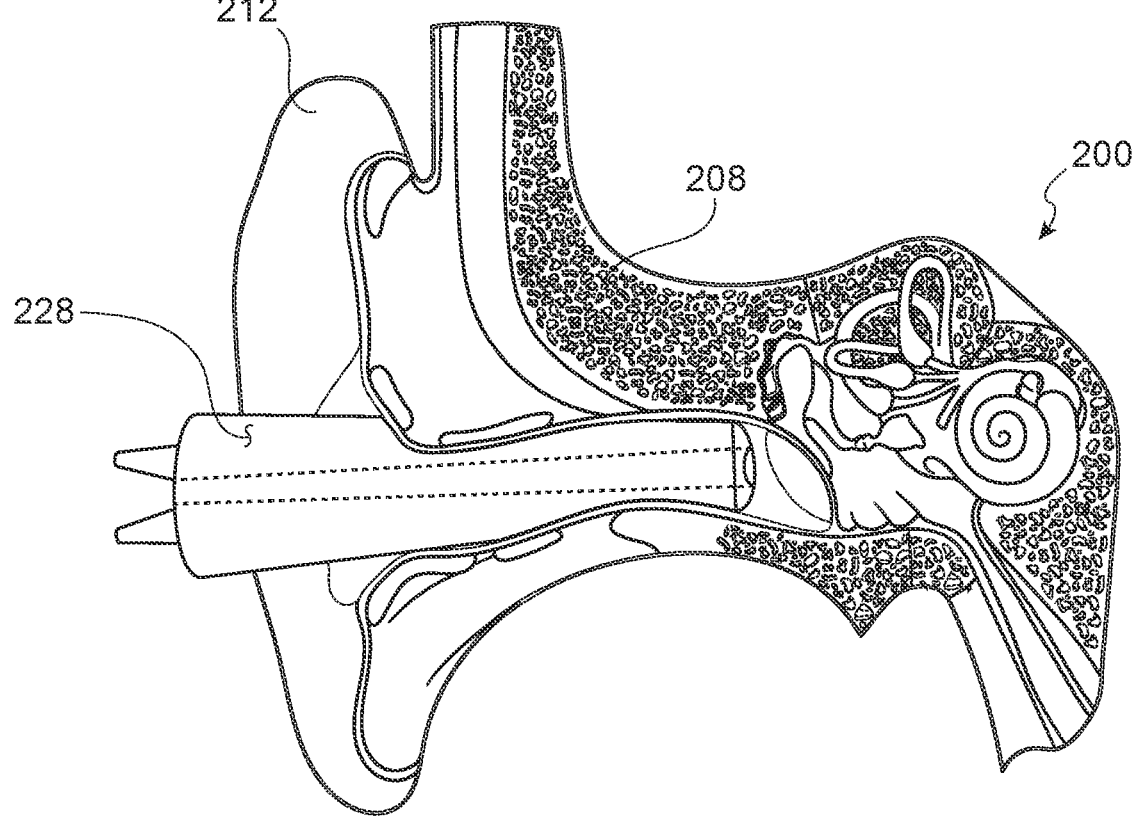
FIG. 5 is a cross-section close-up of an earbud in FIG. 4 installed in an ear canal.
Figure 6:
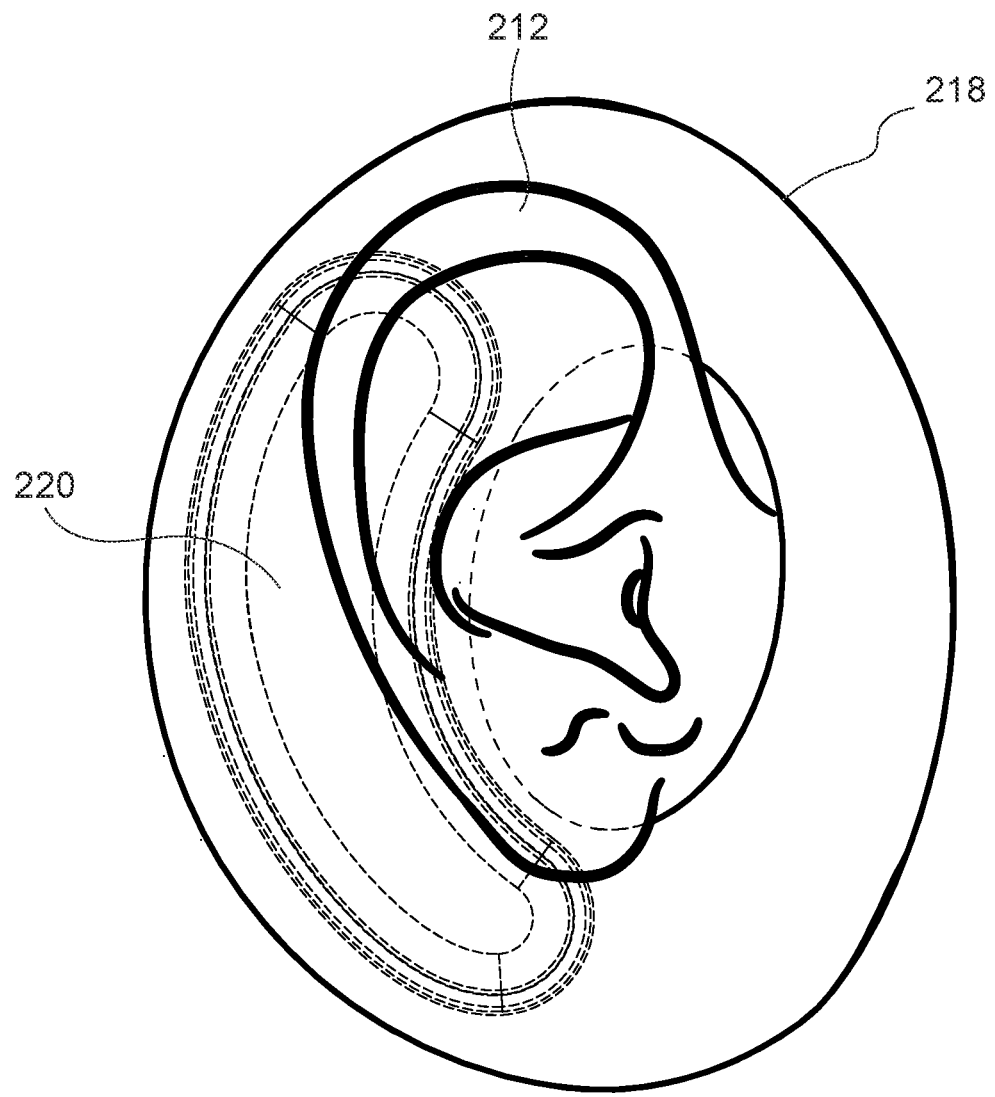
FIG. 6 is a cross-section view through an ear cup installed on the head of a patient.

FIGS. 2 through 4 illustrate an assortment of devices that are operable as transducers 125 to convey thermal energy toward or away from a head of a patient. The headwear 216 in FIGS. 2 and 3 includes ear cups 218 with a heat transfer element 220 particularly configured for installation in the space between a pinna 212 and the temporal bone 28 of a patient. One operable installed arrangement is shown in FIG. 6. In contrast, the transducers 125 in FIG. 4 are configured as ear buds 224 with a heat transfer surface 228 that is inserted into an ear canal, as shown in FIG. 5. A heat transfer zone is formed in the vicinity of contact between a heat transfer element of a transducer and tissue.

In contrast to an exemplary passive ice pack, currently preferred thermal transducers 125 may be characterized as being active. However, certain lesser preferred embodiments may incorporate only one or more passive thermal device. In the latter case, feedback obtained by a portion of a system 100 may be used to control duration or amount of applied thermal therapy in a more manual mode.

An active transducer 125 is desirably controllable to adjust its rate of thermal flow, duration of operation, and/or total amount of transmitted thermal energy. An exemplary thermal transducer 125 may include a thermoelectric device, or circulated fluid from a source of temperature-controlled thermal transfer fluid. A workable thermoelectric device includes a Peltier heat pump.

A process or method of using an embodiment 100 will now be set forth with reference to FIGS. 7 and 8. First, a thermal therapy system 100 is obtained. A workable system 100 includes a thermal transducer 125, a stimulus transducer 120, 135, a receiving transducer 130, and a processing element 145 to integrate and operate the system 100. Thermal transducer 125 is to transmit thermal energy to, or receive thermal energy from, a portion of the head of a human patient in the vicinity of an ear of the patient. Stimulus transmitter 120 or 135 is to impart a stimulus signal to a portion of the head. A stimulus signal can be conducted to an inner ear through air or bone. The receiving transmitter 130 is to detect a signal comprising otoacoustic emission from the ear responsive to the stimulus imparted from a transmitter 120 or 135.

The processing element 145 is disposed in operable connection with the thermal transducer 125, stimulus transmitter 120 and/or 135, and receiving transmitter 130. One function of the processing element 145 is to compare the received signal to a reference. A workable reference can be an averaged empirical result determined by measuring a plurality of comparable "normal" ears' response to a given stimulus. Departure of the received signal from the reference produces a basis from which to inform a corresponding feedback signal. The processing device 145 can be programmed to control any or all aspects of the system 100 based on inputs from one or more transducer, as desired.

A preferred method includes disposing a heat transfer portion of the thermal transducer 125 in operable registration with a temporal bone of the patient; using a stimulus transmitter 120, 135 to impart the stimulus; using the receiving transmitter 130 to receive an otoacoustic signal emitted from the patient; and using the processing element 145 to compare a received signal to the reference and to create a feedback signal. A workable feedback signal can be based at least in-part upon deviation of the received signal from the reference. The feedback signal is then incorporated into operation of at least one element of the system 100 to control application of thermal therapy to the patient.

Figure 7:
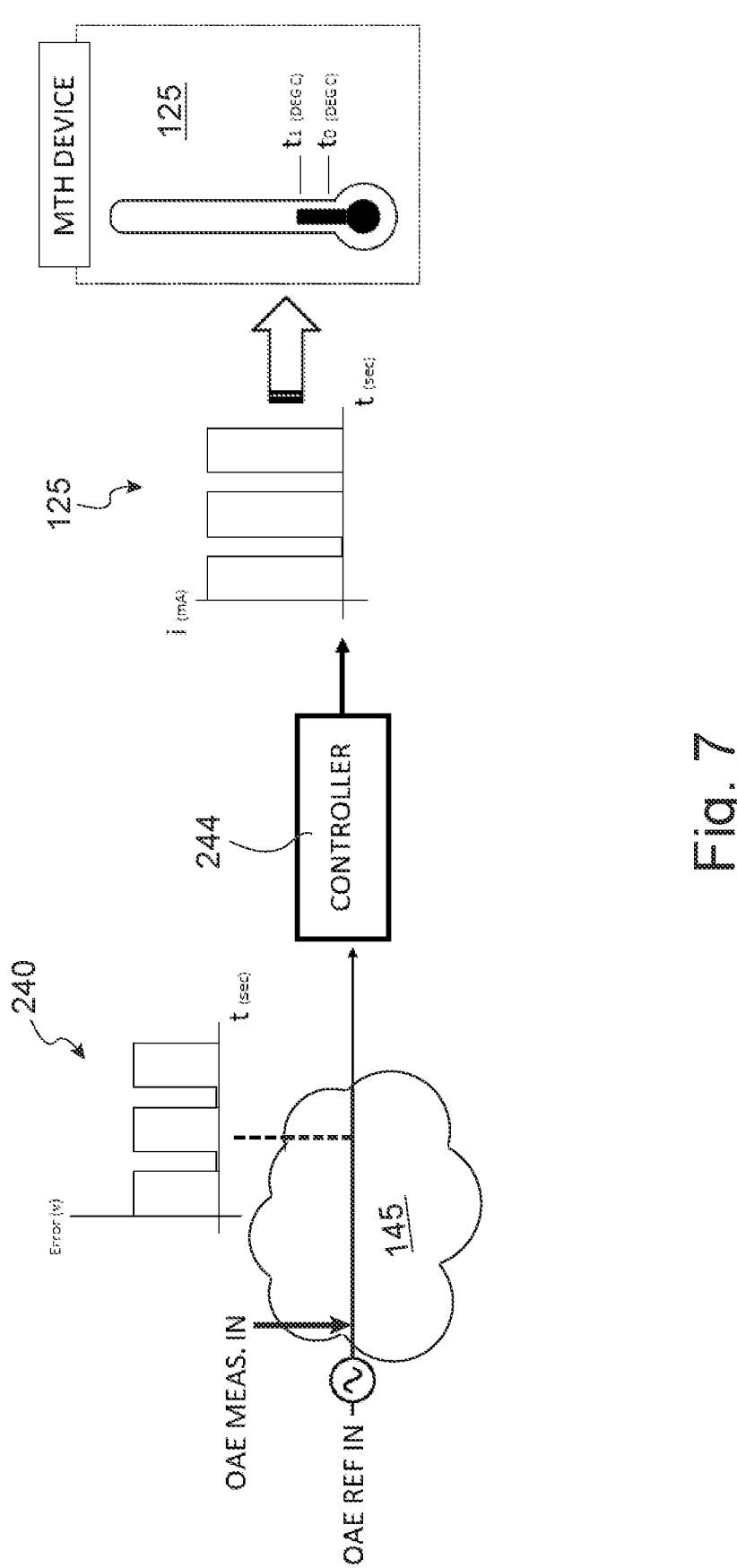
FIG. 7 is a schematic of a control scenario according to certain principles of the invention.

As illustrated in FIG. 7, the error 240 between a received signal and its corresponding reference is relatively large. As a consequence, processor 145 causes controller 244 to output one or more relatively higher amplitude current signals 248 to an electrothermal transducer 125. Subsequently, the temperature in an area of interest is caused (or allowed) to change. With reference to FIG. 8, the discrepancy 240' between a received signal and its corresponding reference is relatively small. As a consequence, processor 145 causes controller 244 to output one or more relatively lower amplitude current signals 248' to an electrothermal transducer 125. Subsequently, the temperature in an area of interest is caused (or allowed) to change.

Figure 8:
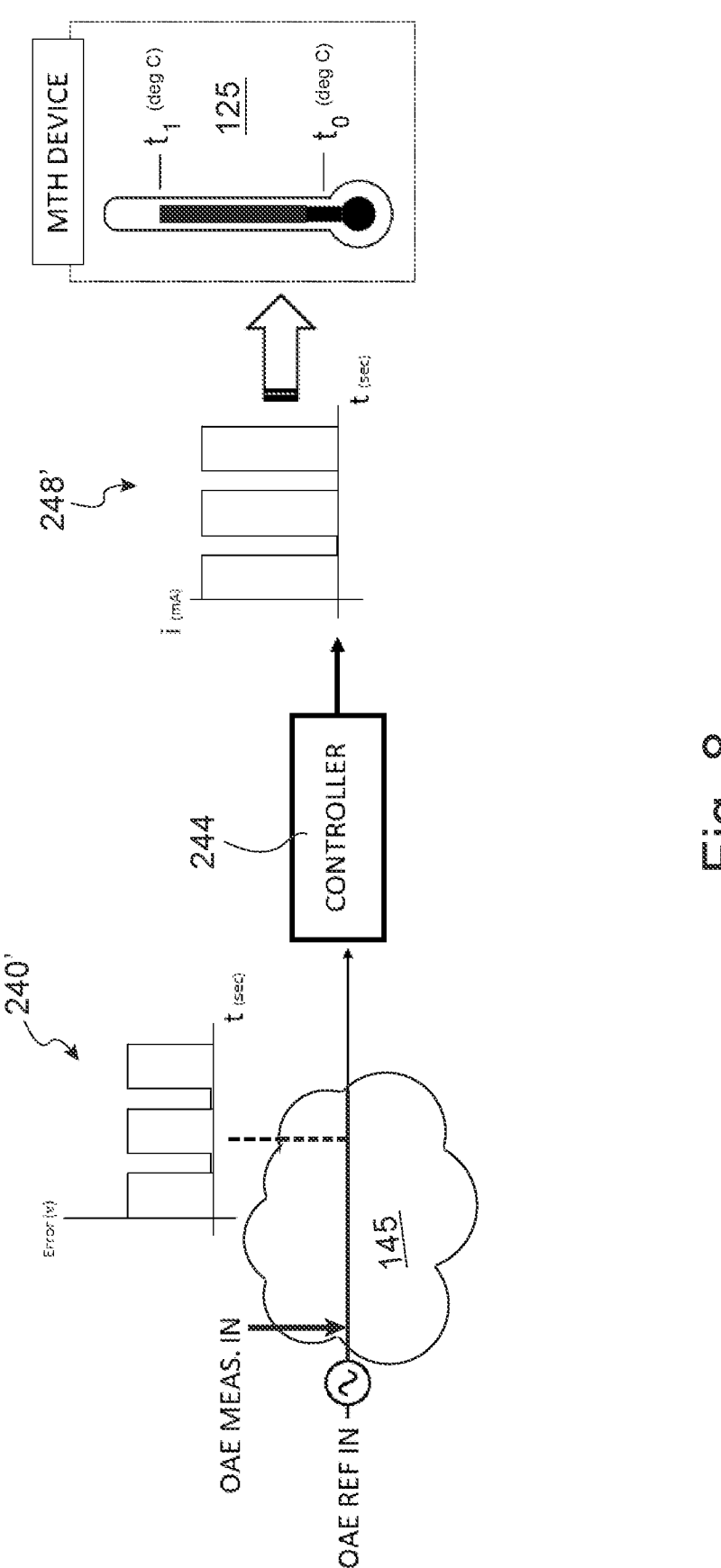
FIG. 8 is a schematic of a control scenario according to certain principles of the invention.

The method illustrated in FIGS. 7 and 8 relates to hypothermia therapy. With reference to FIG. 7, as a therapy session starts, the temperature at the area of interest is reduced by action of controller 244 causing operation current signal(s) 248 having relatively larger amplitude. Large current signals 248 cause an electrothermal transducer 125 to reduce the temperature at an area of interest. As the discrepancy between expected and received signals is reduced over time (presumably by effective action of the therapy), controller 244 is instructed by the processing device to cause operation current signal(s) 248' having relatively smaller amplitude. Consequently, the temperature at the area of applied therapy is increased (or allowed to increase). A thermal therapy session can be essentially autonomous under control of a preprogrammed processing device 145.

Figure 9:
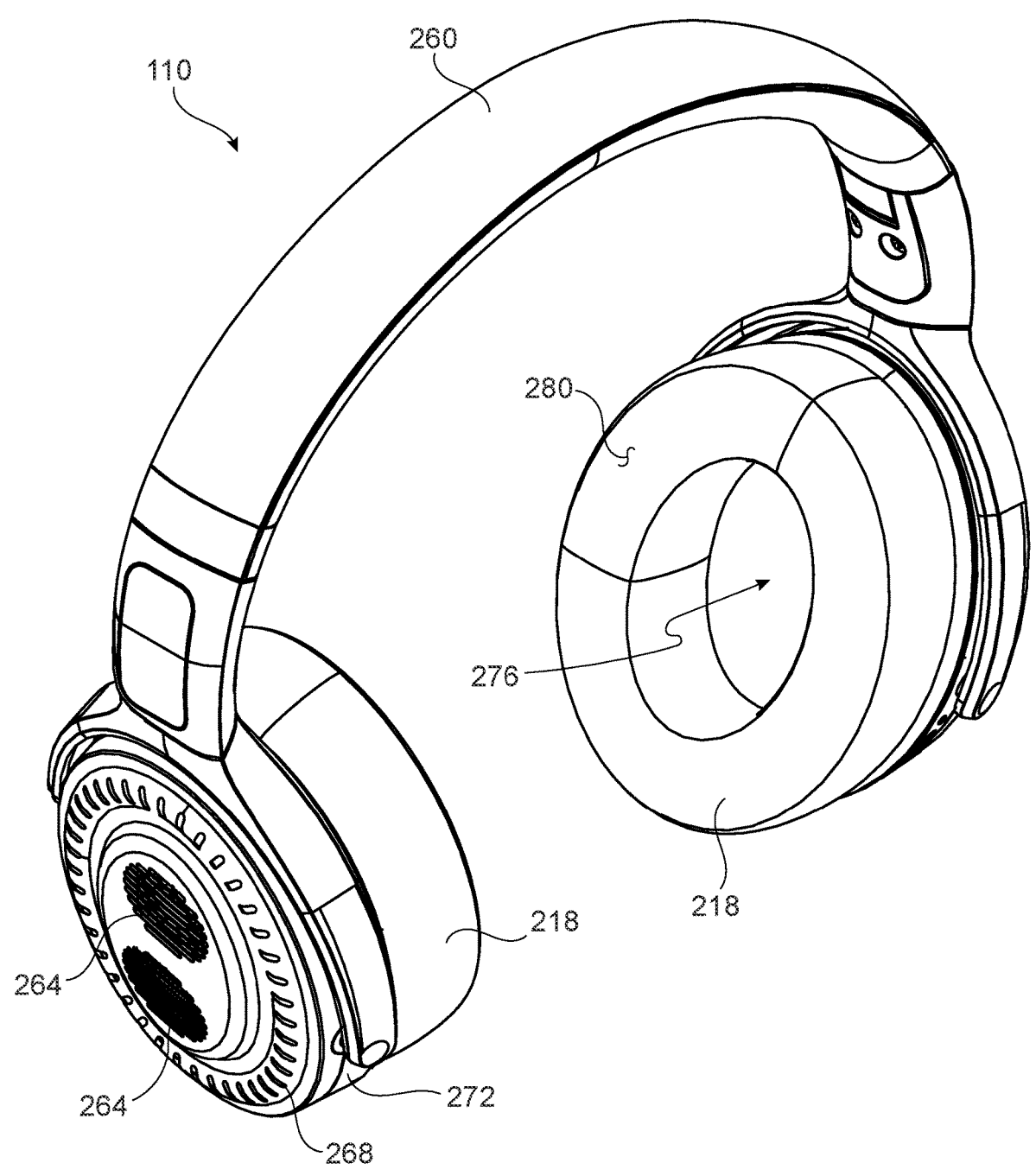
FIG. 9 is a view in perspective of exemplary headwear.

An assembly 110 according to certain principles of the invention is illustrated in FIG. 9. Assembly 110 in FIG. 9 may be characterized as a set of headphones, or headwear. For purpose of this disclosure, the term "headwear" may also encompass an ear bud.

Assembly 110 in FIG. 9 resembles a conventional pair of stereo headphones by including a pair of ear cups 118 held in place on a head by a biased band 260. In addition, one or more ports 264 may be included to facilitate air flow through a portion of the device for thermal management. Additional air ports 268 may also be disposed to further control flow of air through a housing 272 associated with an ear cup 218. A speaker and a microphone are typically disposed in operable registration inside each ear cup 218, as indicated generally at 276. Each ear cup 218 carries at least one heat transferring element. A workable heat transferring element can be coupled to a heat transfer surface 280 to interface with the temporal bone of a wearer.

Figure 10:
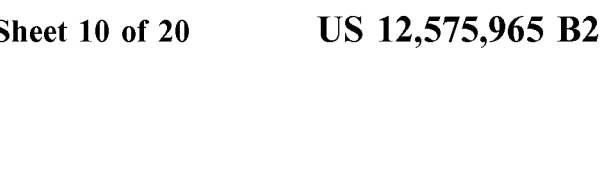
FIG. 10 is an exploded assembly view of the headwear in FIG. 9.
Figure 11:
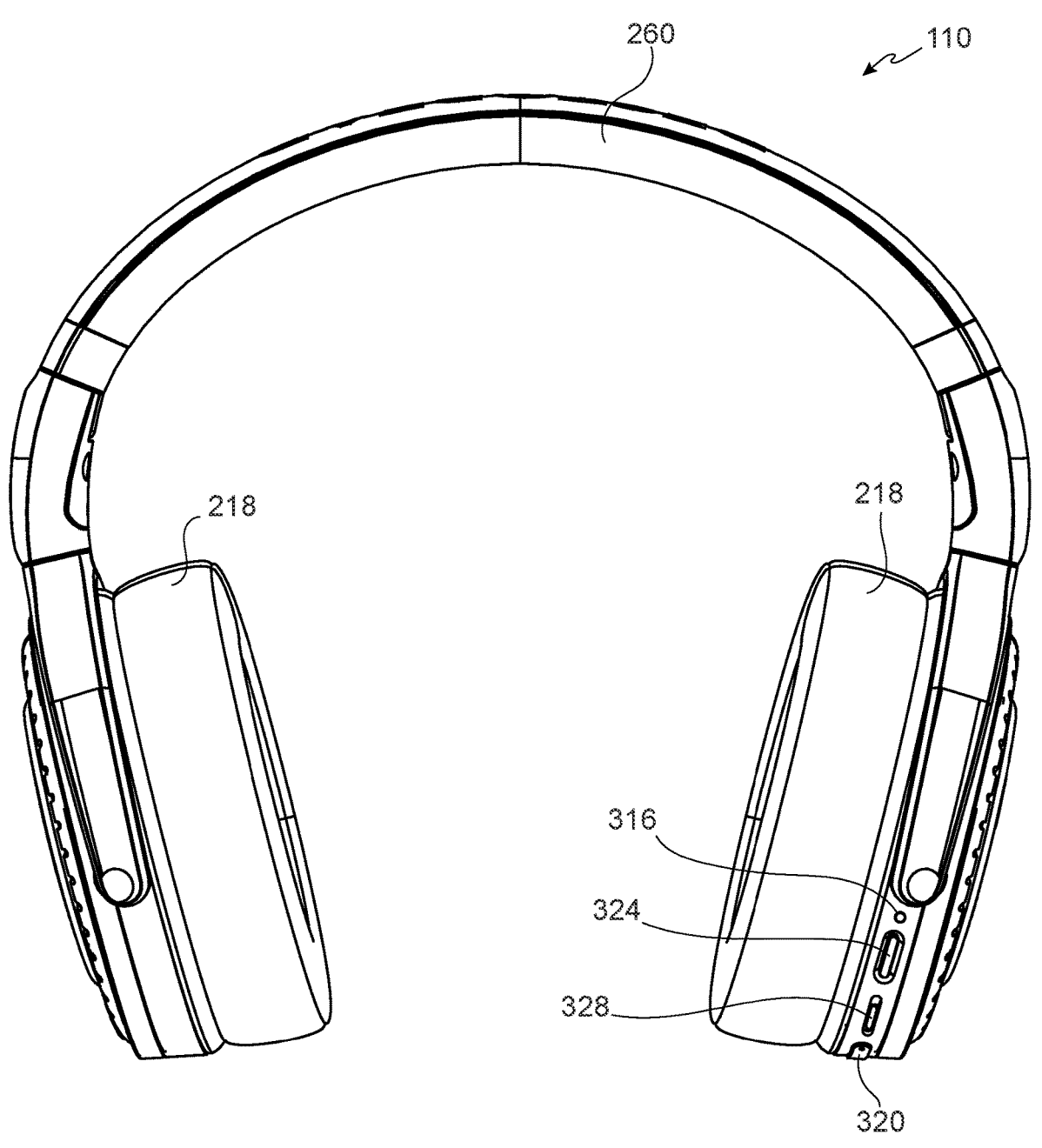
FIG. 11 is a front view of the headwear in FIG. 9.
Figure 12:
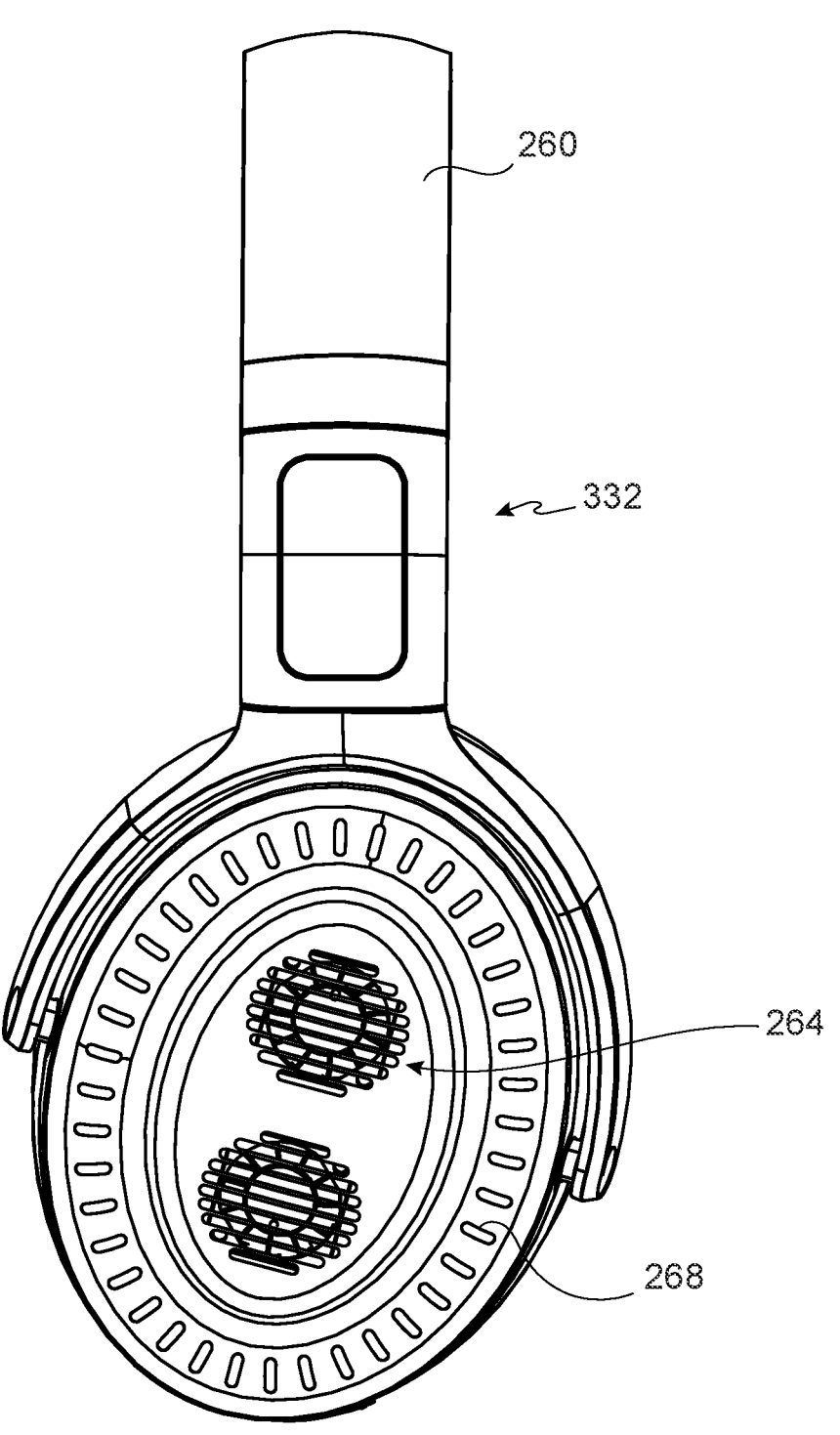
FIG. 12 is a side view of the headwear in FIG. 9.
Figure 13:
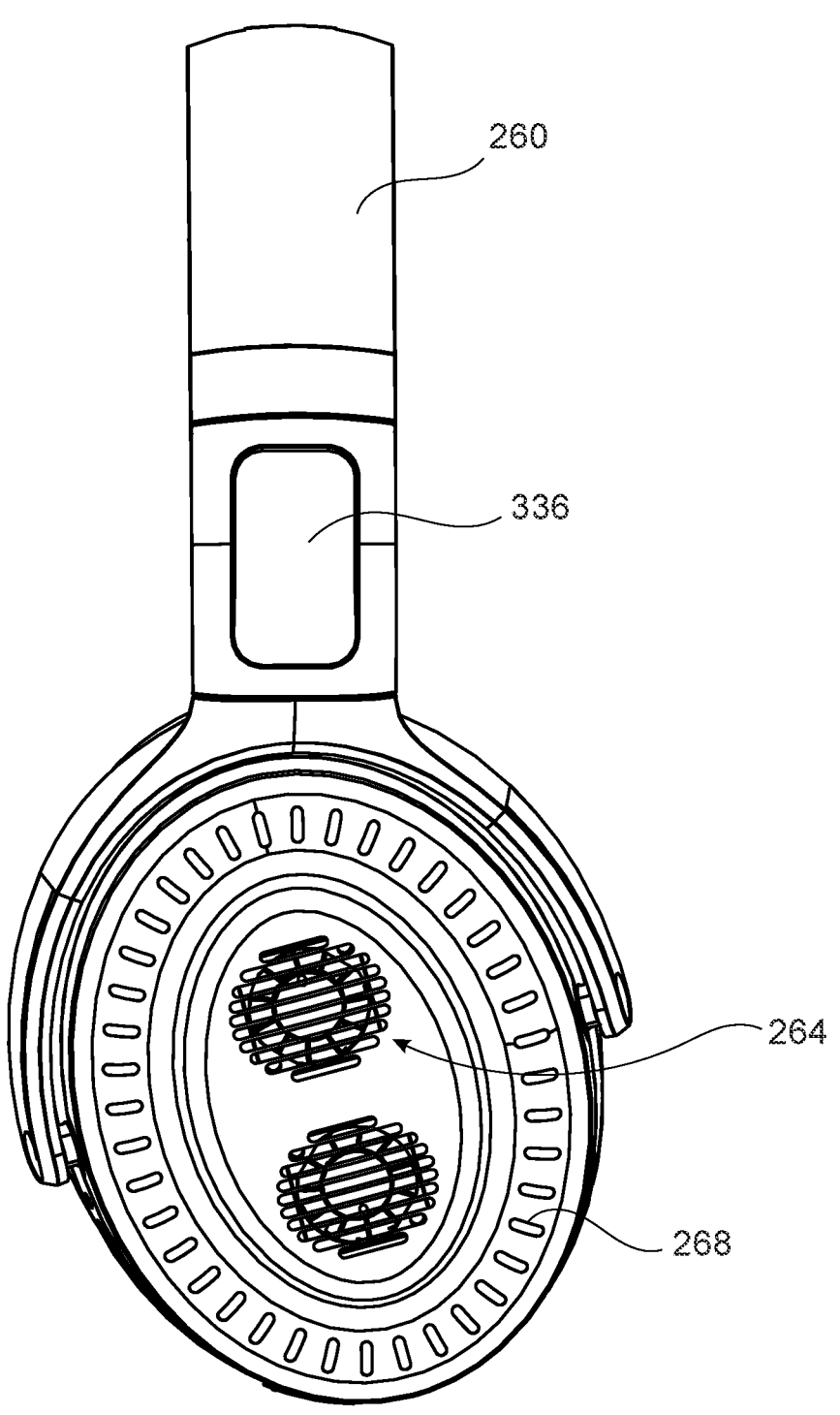
FIG. 13 is a view of the other side of the headwear in FIG. 9.

Details of certain elements that may be carried in an assembly 110 are illustrated in the exploded assembly view of FIG. 10. One or more electrothermal device 284 may be carried on a printed circuit board 288. A heat transfer surface 292 of a thermal device 284 can be configured to cooperate with a heat transfer area of an ear cup 218. A corresponding heat sink 296 can be arranged in an air path from a fan 300. A speaker 304 and microphone 308 are also associated with each ear cup 218. Certain embodiments may also include a microphone 312 arranged to capture ambient sounds for purpose of noise cancelling. With reference to FIG. 11, an embodiment may include one or more of a power indicator 316, an on/off switch 320, and a USB port 328. An optional capacitive touch interface is illustrated generally at 332 in FIG. 12. An optional visual display is indicated generally at 336 in FIG. 13.

Figure 14:
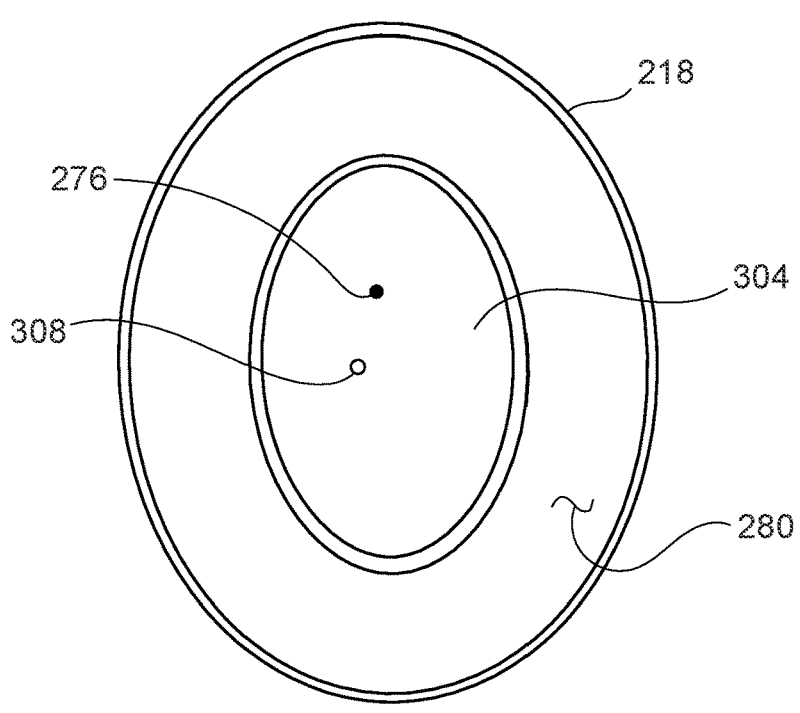
FIG. 14 is a plan view of the patient-contact side of an ear cup.
Figure 15:
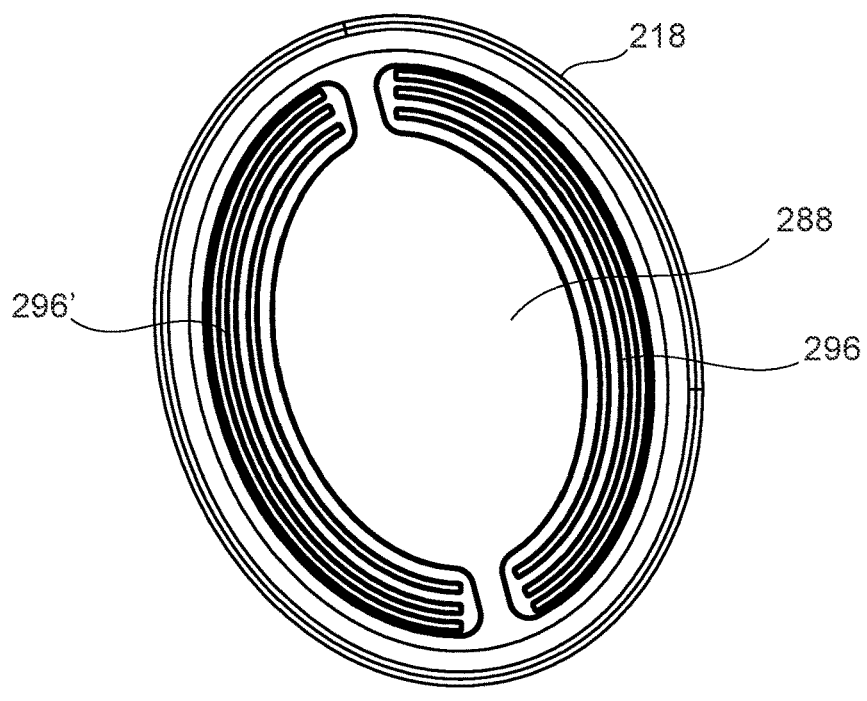
FIG. 15 is a cross-section view of an ear cup.
Figure 20:
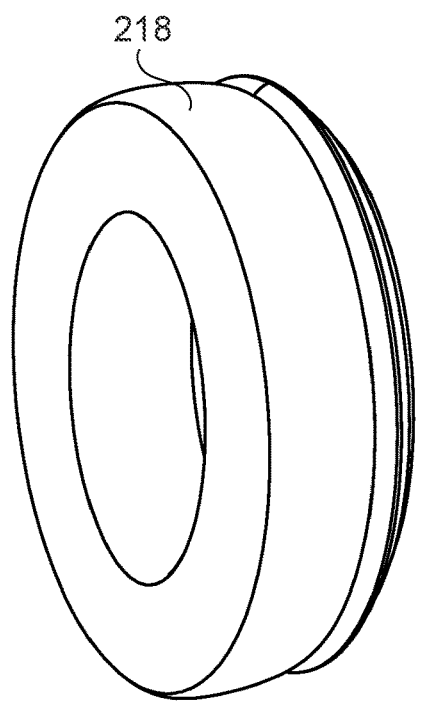
FIG. 20 is a view in perspective of an ear cup.
Figure 21:
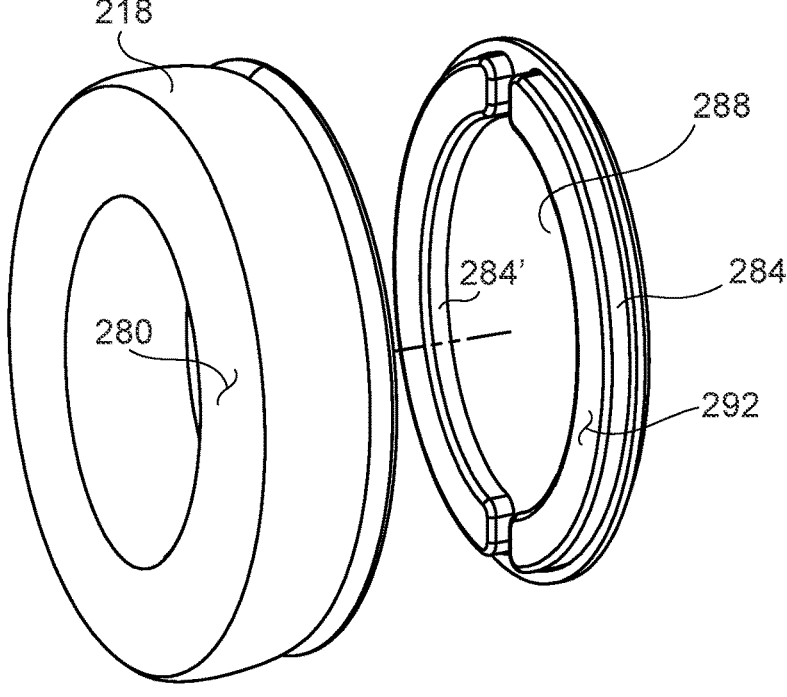
FIG. 21 is an exploded view of the structure illustrated in FIG. 20.
Figures 22, 23, 24, 25, 26:
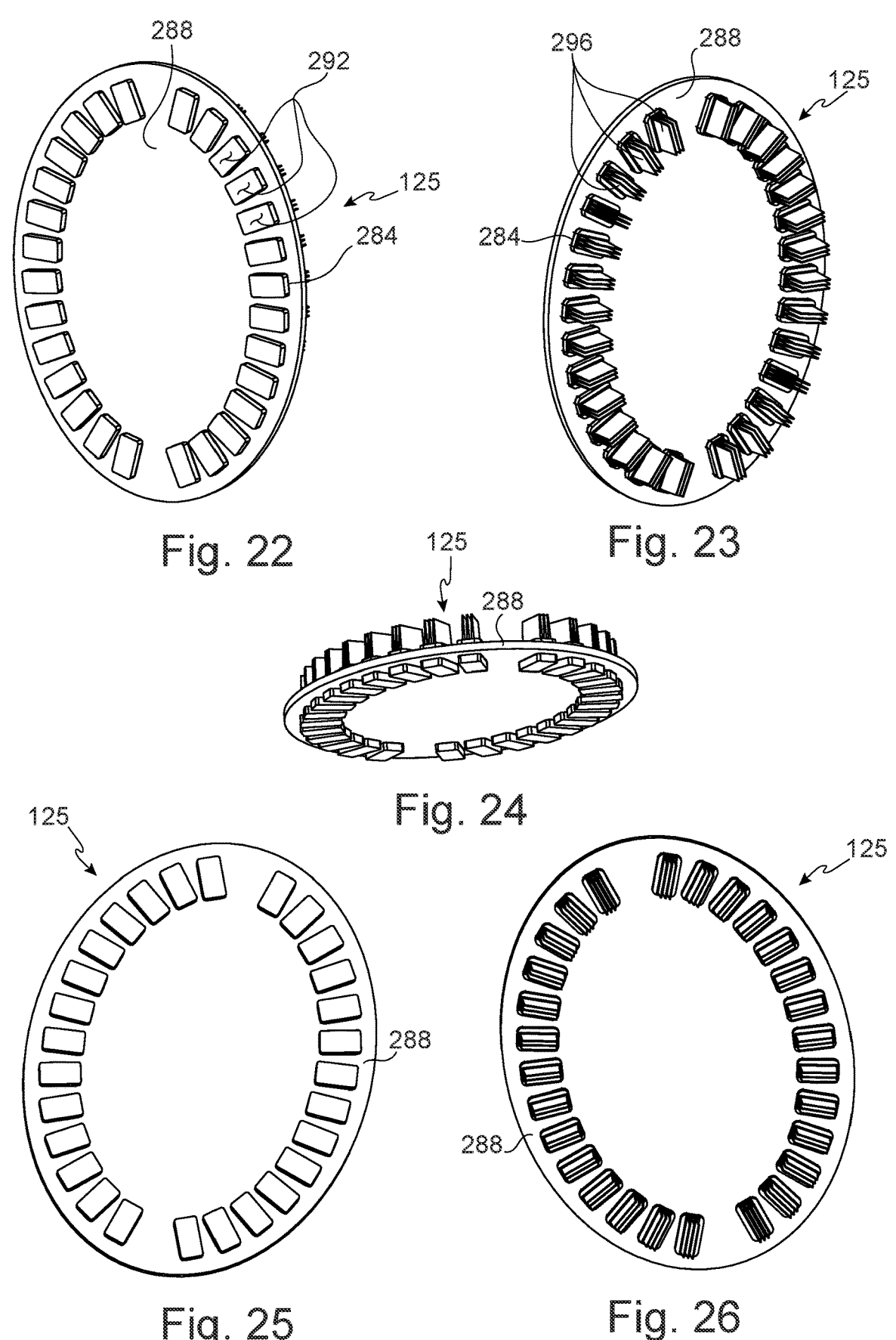
FIGS. 22 through 26 are various perspective views of an alternative thermal transduce and PCB.

FIGS. 14 and 15 illustrate front and rear views of partially assembled ear cups 218. As clearly illustrated in FIG. 15, a plurality of heat transfer elements may be included in a single ear cup (e.g., thermoelectric elements 296 and 296'). A plurality of heat transfer devices, or the degree of partial arcuate coverage of one or more elements in a group, can allow a tailored heat transfer profile to be applied to a head. FIGS. 16 and 17 illustrate front and rear views of a printed circuit board (PCB) carrying a pair of heat transfer elements 284. FIGS. 18 and 19 illustrate perspective views of the same elements. FIGS. 20 and 21 illustrate assembly of the PCB 288 into an ear cup 218 to locate surface 292 in operable harmony with surface 280.

Figure 27:
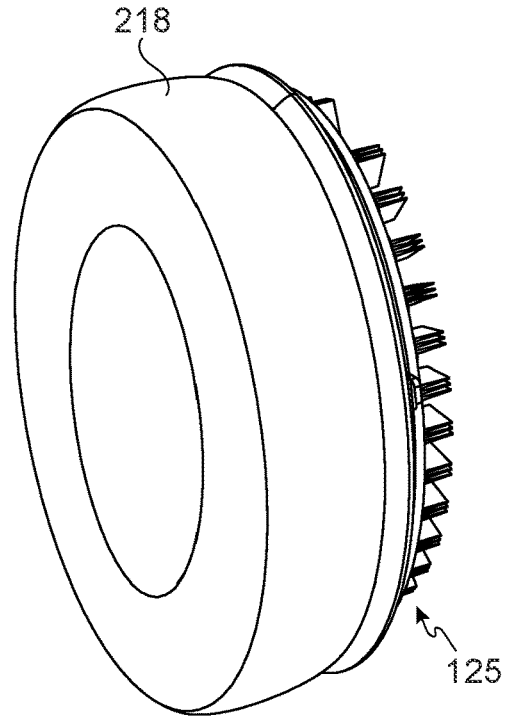
FIG. 27 is a view in perspective of an alternative ear cup.
Figure 28:
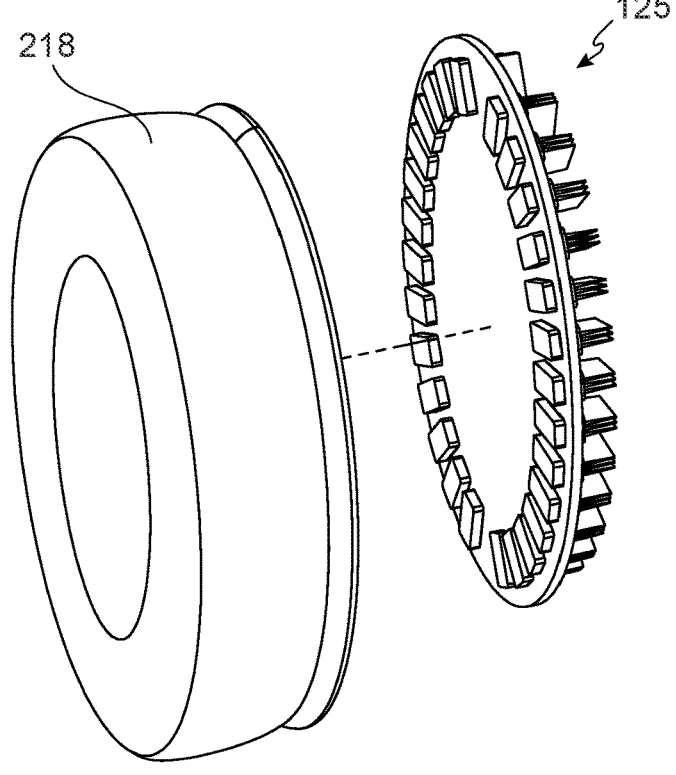
FIG. 28 is an exploded view of the structure illustrated in FIG. 27.

FIGS. 22 through 26 illustrate various perspective views of an alternative arrangement of a workable thermal transducer 125. As illustrated, a collection of individual thermoelectric devices may be arranged to populate a heat transfer area. An advantage of such arrangement is the ability to selectively energize one or more device 284 at the same time. Consequently, a variable heat transfer profile may be applied to a patient. FIGS. 27 and 28 are similar to FIGS. 20 and 21, and illustrate an assembly step to couple the alternative thermal transducer 125 to an ear cup 218.

8

Figure 29:
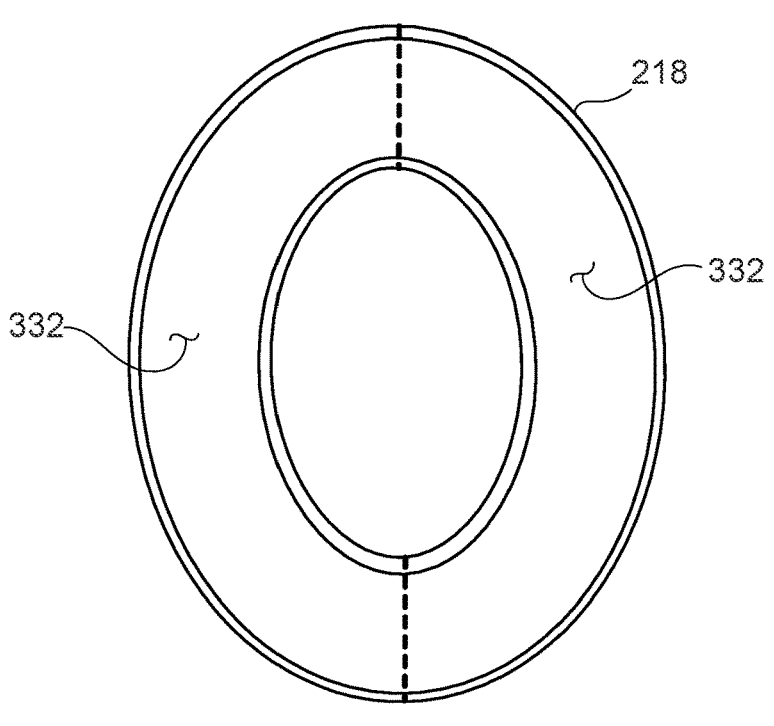
FIGS. 29 and 30 are plan views of the patient-contact portions of ear cups.
Figure 30:
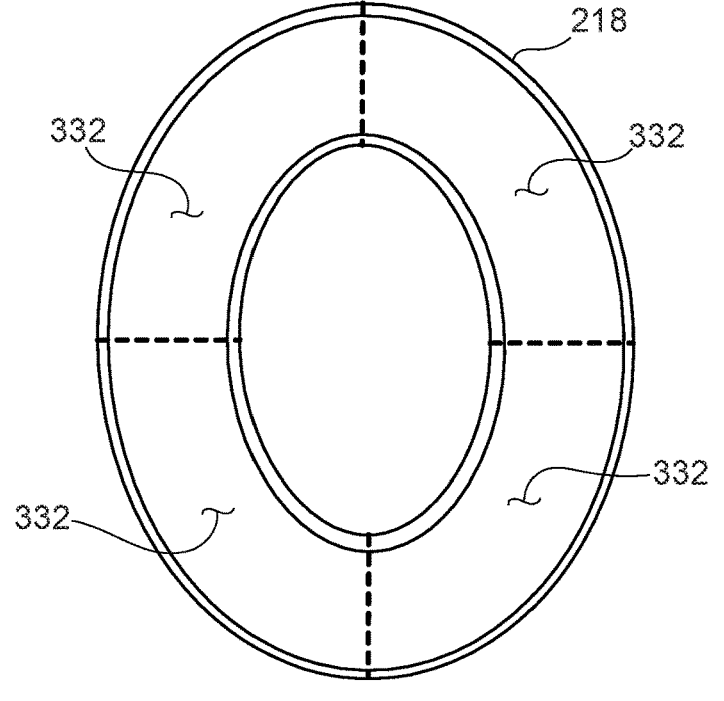

FIG. 29 illustrates the case where the thermal transducer arrangement is configured to establish two heat transfer zones 332. For example, the illustration in FIG. 29 may correspond to an arrangement of heat transfer zones or areas 332 produced by the thermal transducers 125 in FIGS. 16 through 19. It may be envisioned that appropriately energizing certain members of the family of transducers 284 in FIGS. 22 through 26 may produce an equivalent result. A four-zone heat transfer arrangement is illustrated in FIG. 30. The number and shape of potential zones or areas 332 is set by the number and distributed conformation of individual heat transfer transducers 284.

Figure 31:
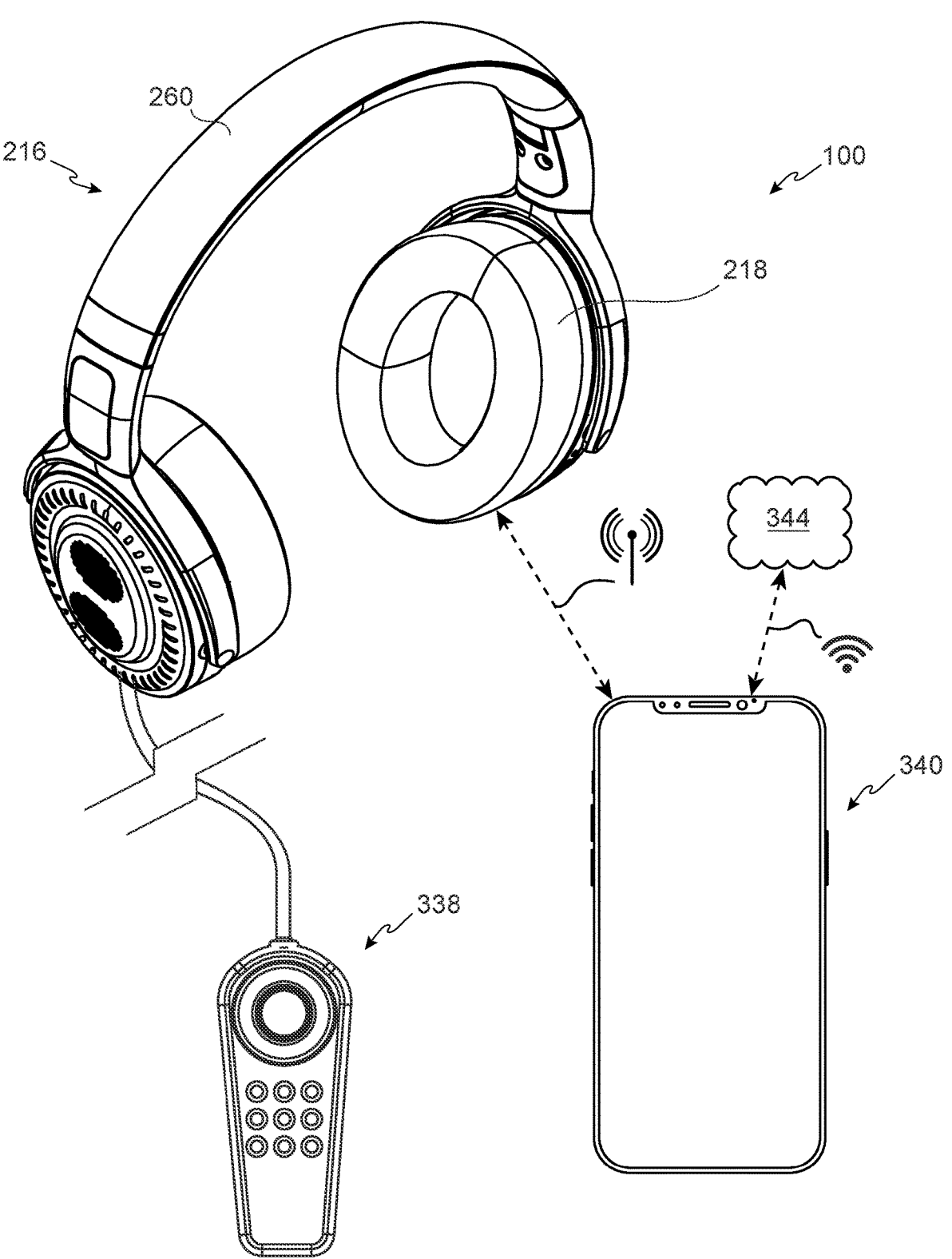
FIG. 31 is a schematic of a system according to certain principles of the invention.

An embodiment 100 that may be used in accordance with certain principles of the invention is illustrated in FIG. 31. Headwear 216 is provided to associate at least one thermal transducer 125 with each ear of a patient. Each ear cup 218 of the headwear carries a microphone to receive otoacoustic emission responsive to a stimulus imparted to the patient. The headwear 216 also carries at least one of a transducer 120 and/or 135 to impart the stimulus signal through air (sonically) or through bone conduction (mechanically) to a patient. Elements associated with the headwear may be controlled by on-board controls (as discussed above), or may be controlled by a tethered control interface, generally 338. A workable control interface 338 may alternatively communicate with the headwear wirelessly. A hand-held computing device, generally 340, may be operably coupled with the headwear 216. Either of the control interface 338 or hand-held device 340 may be used to perform computations, compare OAE to an expected reference, acquire data from one or more transducer, energize a heat transducer for a programmed interval, modify a treatment regime according to collected data, and the like. Communication to one or more remote transducer 344 (e.g., for collection of data related to EKG, skin moisture content, temperature, and the like) may be by way of wired or wireless connectivity to a respective device.

Although the invention has been described with regard to certain preferred embodiments, the scope of the invention is to be defined by the appended claims.

What is claimed is:

1. A method, comprising:
providing a thermal therapy system, the system comprising:
headwear carrying a device to transmit thermal energy to, or receive thermal energy from, a portion of the head of a human patient in the vicinity of an ear of the patient;
a transmitter to impart a first signal to a portion of the head; and
a first receiver to detect a second signal comprising acoustic emission from the ear;
installing the headwear onto the head of the patient to dispose a heat transfer area of the device in operable registration with a temporal bone of the patient;
using the transmitter to impart the first signal;
using the first receiver to monitor for presence of the second signal;
comparing a received second signal to a first reference to create a first feedback signal based at least in-part upon deviation of the received second signal from the first reference; and
incorporating the first feedback signal into operation of the system to apply thermal therapy to the patient.

2. The method of claim 1, wherein:

the first reference comprises expected stimulus frequency OAE, expected transient-evoked OAE, or expected distortion product OAE.

3. The method of claim 1, wherein:

the system further comprises a second receiver capable of detecting a third signal, the third signal to indicate a state or condition of a physiologic variable selected from the group consisting of heart rate, blood pressure, EKG/ECG, body or skin temperature, blood/oxygen saturation, and skin moisture; and the method further comprises acquisition of the third signal and comparison of the third signal to a corresponding physiologic metric reference to modify the first feedback signal or to create a second feedback signal for operation of the system based in-part upon deviation of the received third signal from the corresponding physiologic metric reference.

4. The method of claim 3, wherein:

the second feedback signal is used by the system as a control input for injection of a chemical agent into the patient; and the method further comprises using the system to inject the chemical agent into the patient.

5. The method of claim 3, further comprising:

modifying thermal therapy applied to the patient based, in-part, on departure of the second signal or the third signal from its corresponding reference over a period of time.

6. The method of claim 1, wherein:

the first signal comprises a sound wave transmitted through air.

7. The method of claim 1, wherein:

the first signal is applied by the transmitter to structure of the head for conduction into the ear through a solid medium.

8. The method of claim 1, wherein:

the step of installing the headwear onto the head of the patient comprises disposing a thermal conveyance portion of the device in contact with an area located between a pinna of the patient and the patient's skull.

9. The method of claim 1, wherein:

the step of installing the headwear onto the head of the patient comprises folding a pinna of a patient's ear to facilitate placement an ear cup of headwear in engagement around a portion of the ear.

10. A method, comprising:

providing a thermal therapy system, the system comprising:

a device to transmit thermal energy to, or receive thermal energy from, a portion of the head of a human patient in the vicinity of an ear of the patient;

a transmitter to impart a stimulus to a portion of the head;

a receiver to detect a signal comprising acoustic emission from the ear responsive to the stimulus; and a processing element disposed in operable connection with the device, transmitter, and receiver to compare the signal to a reference;

disposing a heat transfer portion of the device in operable registration with a temporal bone of the patient;

using the transmitter to impart the stimulus;

using the receiver to receive the signal;

using the processing element to compare a received signal to the reference and create a feedback signal, the feedback signal being based at least in-part upon deviation of the received signal from the reference; and incorporating the feedback signal into operation of the system to control application of thermal therapy to the patient.

11. An apparatus, comprising:

a device to cause flow of thermal energy toward or away from a portion of the head of a human patient in the vicinity of an ear of the patient;

a transmitter to impart a first stimulus signal to a portion of the head;

a first receiver to detect a second signal comprising acoustic emission (OAE) from the ear responsive to the first signal; and a processor disposed in-circuit with the device, transmitter, and receiver, the processor to regulate flow of thermal energy between the device and the patient based at least in-part on a discrepancy between the second signal and a reference.

12. The apparatus of claim 11, wherein:

the device is configured to provide a controllable flow rate or amount of thermal energy for transfer to or from the head.

13. The apparatus according to claim 11, wherein:

the device is an integral portion of headwear.

14. The apparatus according to claim 13, wherein:

the headwear is configured upon installation to dispose an ear pinna inside an ear cup such that a portion of a heat transfer element of the device is disposed between the pinna and a temporal bone of the patient.

15. The apparatus according to claim 13, wherein:

the device comprises an electrically controllable thermal source or sink.

16. The apparatus according to claim 13, wherein:

the device comprises a plurality of thermal sources or sinks configured to at least partially circumscribe an ear canal of the patient.

17. The apparatus according to claim 16, wherein:

a plurality of the thermal sources or sinks are individually controllable.

18. The apparatus according to claim 11, wherein:

the device is configured to provide a heat transfer zone disposed inside an ear canal.

19. The apparatus according to claim 13, wherein:

the headwear further carries the transmitter and first receiver.

20. The apparatus according to claim 11, wherein:

the apparatus comprises a dosing mechanism to dispense a therapeutic drug to the patient.

\* \* \* \* \*